(12) United States Patent
Brustad

(10) Patent No.: US 8,500,695 B2
(45) Date of Patent: *Aug. 6, 2013

(54) SURGICAL ACCESS DEVICE WITH FLOATING GEL SEAL

(75) Inventor: John R. Brustad, Dana Point, CA (US)

(73) Assignee: Applied Medical Resources Corporation, Rancho Santa Margarita, CA (US)

(*) Notice: Subject to any disclaimer, the term of this patent is extended or adjusted under 35 U.S.C. 154(b) by 324 days.

This patent is subject to a terminal disclaimer.

(21) Appl. No.: 13/007,210

(22) Filed: Jan. 14, 2011

(65) Prior Publication Data
US 2011/0112480 A1 May 12, 2011

Related U.S. Application Data

(63) Continuation of application No. 12/693,860, filed on Jan. 26, 2010, now Pat. No. 7,883,493, which is a continuation of application No. 11/753,752, filed on May 25, 2007, now Pat. No. 7,651,478, which is a continuation of application No. 10/056,831, filed on Jan. 24, 2002, now Pat. No. 7,235,062.

(51) Int. Cl.
A61M 5/178 (2006.01)

(52) U.S. Cl.
USPC ...................................... 604/167.02

(58) Field of Classification Search
USPC ................. 604/167, 280, 256, 249, 264, 160, 604/161
See application file for complete search history.

(56) References Cited

U.S. PATENT DOCUMENTS

| 4,895,565 | A | 1/1990 | Hillstead |
| 5,209,737 | A | 5/1993 | Ritchart et al. |
| 5,360,417 | A | 11/1994 | Gravener et al. |
| 5,385,553 | A | 1/1995 | Hart et al. |
| 5,407,433 | A | 4/1995 | Loomas |
| 5,411,483 | A | 5/1995 | Loomas et al. |
| 5,429,609 | A | 7/1995 | Yoon |
| 5,441,486 | A | 8/1995 | Yoon |
| 5,634,908 | A | 6/1997 | Loomas |
| 5,788,676 | A | 8/1998 | Yoon |
| 5,820,606 | A | 10/1998 | Davis et al. |
| 5,865,807 | A | 2/1999 | Blake, III |
| 7,235,062 | B2 * | 6/2007 | Brustad ................... 604/167.02 |

* cited by examiner

Primary Examiner — Manuel Mendez
(74) Attorney, Agent, or Firm — Patrick Y. Ikehara

(57) ABSTRACT

A trocar is provided with a cannula and a housing and valve assembly disposed in the housing which forms a housing seal, and instrument seal, and in some cases a zero seal. A gel material is included in the valve and provides the valve with superior flotation properties for maintaining the instrument seal even when the instrument is moved off-axis. In order to accommodate movement of the gel material, voids can be formed within the valve housing and even within the gel material.

18 Claims, 4 Drawing Sheets

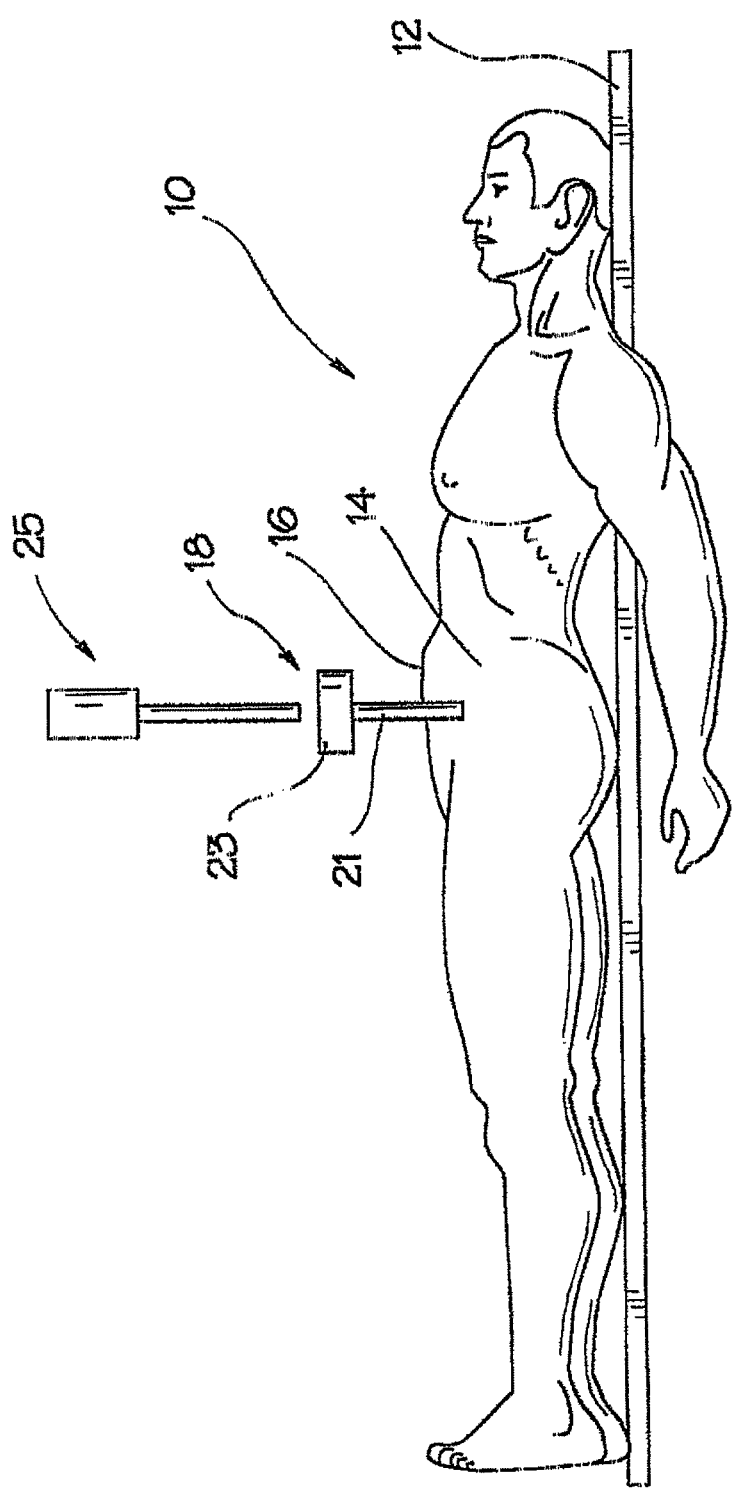

SURGICAL ACCESS DEVICE WITH FLOATING GEL SEAL

CROSS-REFERENCE TO RELATED APPLICATION

This application is a continuation of U.S. application Ser. No. 12/693,860, filed Jan. 26, 2010, which is a continuation of U.S. application Ser. No. 11/753,752, filed May 25, 2007, now U.S. Pat. No. 7,651,478, which is a continuation of U.S. application Ser. No. 10/056,831, filed Jan. 24, 2002, now U.S. Pat. No. 7,235,062, all the disclosures of which are incorporated by reference in their entireties.

BACKGROUND OF THE INVENTION

1. Field of the Invention

This invention relates generally to surgical access devices and more specifically to valves and seals associated with such devices.

2. Discussion of the Related Art

Access devices are commonly used to facilitate the introduction of surgical instruments into body conduits and body cavities. One such device, which is typically referred to as a trocar, is used in laparoscopic procedures to provide access through the abdominal wall and into the abdominal cavity. In laparoscopic surgeries, the abdominal cavity is commonly inflated or insufflated in order to increase the volume of the working environment. Under these circumstances, valves are provided in a valve housing of the trocar to inhibit the escape of the insufflation gas. The valves form an instrument seal in the presence of an instrument, and a zero seal in the absence of an instrument.

Trocar seals are disclosed and claimed in applicant's U.S. Pat. No. 5,385,553, which is incorporated herein by reference. This patent discusses the problems which can be encountered when the instrument is inserted off-axis. The solution of floating the valve is discussed in detail.

In this patent it is contemplated that the valve would comprise first portions which define an orifice through the valve and second portions disposed outwardly of the first portions. These second portions are intended to provide a greater flexibility than the first portions. As a consequence, when an instrument is inserted off-axis, the second portions will deform while the first portions, which form the instrument seal, will remain undeformed. One of the embodiments contemplates provision of an excess of material disposed outwardly of the valve orifice which functions generally as a bellows. In this case the first portions of the valve have a first radial length to radial distance ratio while the second portions of the valve have a second radial length to radial distance ratio. The valving mechanism is formed generally of a solid but elastomeric material.

SUMMARY OF THE INVENTION

In accordance with the present invention, an access device is provided, for example, in the form of a trocar having a valve housing. In this case, a valve assembly is disposed in the housing and includes a gel material which has superior sealing characteristics and flotation properties. In some respects, the gel is a solid in that it has a generally fixed volume. On the other hand, the gel functions somewhat like a liquid in that it tends to "flow." Other characteristics of the gel material, such as an elongation greater than 1000 percent, a low durometer and an excellent tear strength are disclosed and claimed in applicant's International Application No. PCT/US01/29682. This application, which was filed on Sep. 21, 2001 and entitled "Surgical Access Apparatus and Method", is incorporated herein by reference.

The gel material will typically form a seal with the valve housing and may also be used to form the instrument seal as well as the zero seal. Alternatively, the valve assembly can be formed with a typical septum valve supported by the gel material to provide the septum valve with the superior flotation properties.

In order to facilitate compression of the gel material, voids can be created in the housing or even within the gel material to accommodate compression of the material during insertion of an instrument.

Aspects of the Invention

In one aspect of the invention, a trocar has an axis and is adapted to provide access for a surgical instrument across a body wall and into a body cavity. A cannula, disposed along the axis, has a proximal end and a distal end, and is adapted for disposition across the body wall. A housing disposed along the access at the proximal end of the cannula is adapted to receive the surgical instrument and to introduce the instrument into the cannula. A valve is disposed in the housing and provided with properties for forming a first seal with the housing wall, a second seal with the instrument when it is present in the trocar and a third seal with itself when the instrument is absent from the trocar. A gel material included in the valve has flotation properties for maintaining the second seal even when the surgical instrument is moved laterally of the axis of the trocar.

In another aspect of the invention, a valve assembly includes a septum valve disposed in the valve housing and adapted to form a first seal with the instrument when it is received into the trocar. A valve support is disposed between the septum valve and the housing to float the septum valve relative to the housing. The valve support includes a gel having elongation greater than 1000 percent to facilitate maintenance of the first seal during off-axis movement of the instrument relative to the housing. The septum valve can be insert molded to the valve support. In another aspect of the invention, a valve is disposed in the valve housing and adapted to form a seal with the instrument when the instrument is inserted through the valve housing and into the cannula. Portions of the valve include a gel material having properties for moving relative to the axis to maintain the seal with the instrument when the instrument is moved off-axis.

Voids can be formed in proximity to the gel material to facilitate movement of the material relative to the axis. These voids can be formed primarily on the walls of the valve housing, between the walls and the gel material and even within the gel material.

These and other features and advantages of the invention will become more apparent with a description of preferred embodiments in reference to the associated drawings.

DESCRIPTION OF THE DRAWINGS

FIG. 1 is a side elevation view of a patent operatively position with a trocar extending into the abdominal cavity and providing access for a surgical instrument;

DETAILED DESCRIPTION OF CERTAIN EMBODIMENTS AND BEST MODE OF THE INVENTION

Figure 2A:
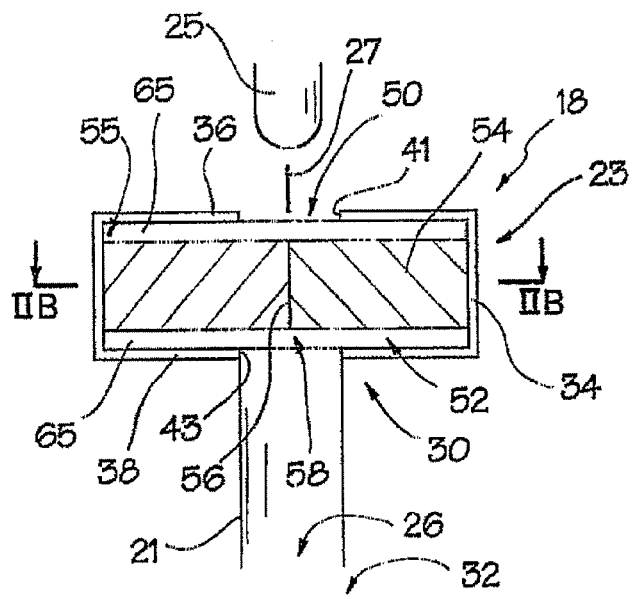
FIG. 2A is an axial cross section view of one embodiment of the trocar, and illustrates a zero seal configuration in the absence of the instrument.

A patient is illustrated in FIG. 1 and designated generally by the reference numeral 10. The patient 10 is illustrated in a prone position on an operation table 12 where he is prepared for laparoscopic surgery. This type of surgery is performed within the patient's abdominal cavity 14 with minimal access through an abdominal wall 16. This access is typically provided by a trocar 18 having a cannula 21 and valve housing 23. The trocar 18 may be one of several trocars which are used simultaneously to provide access for surgical instruments such as the instrument 25 illustrates in the form of a laparoscope.

During a laparoscopic procedure the abdomen 14 is typically inflated with an insufflation gas, such as carbon dioxide, in order to distend the abdominal wall 16 and thereby increase the volume of the working environment. It is the purpose of the valve housing 23 and associated valves to maintain this insufflation gas within the abdominal cavity 14, both in the presence of the instrument 25 and in the absence of the instrument 25.

One embodiment of the trocar 18 of the present invention is illustrated in FIG. 2. In this detailed view, the trocar 18 is shown to include the cannula 21 with a working channel 26 (extending generally along an axis 27), a proximal end 30, and a distal end 32. The valve housing 23 is coupled to the distal end 32 in coaxial alignment with the cannula 21.

In this embodiment, the valve housing 23 is constructed with a cylindrical, vertical wall 34 and a pair of generally annular horizontal walls 36 and 38. The wall 36 can be disposed generally perpendicular to the axis 27 with portions defining an exterior opening 41 for instrument access.

In the illustrated embodiment, the wall 38 is generally parallel to the wall 36 and defines an interior opening 43 which communicates with the working channel (26) of the cannula 21.

A valve assembly 50 is illustrated within the valve housing 23 but could be disposed anywhere along the axis 27. The valve assembly 50 includes a block 52 of gel material 54. In this embodiment, the block 50 forms a housing seal 55 with the vertical wall 34 to prevent the leak of insufflation gases between the gel material 54 and the housing 23. The gel block 52 is further configured with a slit or opening 56 which in this embodiment extends along the axis 27. This opening 56 is perhaps best illustrated in the cross sectional views of FIGS. 2A and 2B.

Figure 2B:
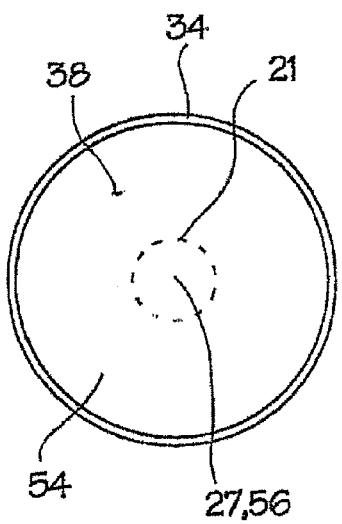
FIG. 2B is a cross section view taken along lines IIB-IIB of FIG. 2A.

In FIG. 2A, the valve assembly 50 is illustrated in the absence of the instrument 25 (FIG. 1). Under these circumstances, the gel material 54 closes the opening 56 to form a zero seal 58. The zero seal 58 in this embodiment is formed solely by the gel material 54, generally along the axis 27, and prevents the escape of insufflation gases through the gel block 52 in the absence of the instrument 25.

The gel block 52 is not merely a septum having only a thin dimension along the axis 27. Rather, the block 52 is preferably formed so that the ratio of its thickness to its outermost dimension, such as its radius, is in a range between one and five. The thickness of the block 52 is preferably in a range between five and ten millimeters. In a preferred embodiment, the gel block 52 in the relaxed state shown in FIG. 2A, has a thickness of about seven millimeters and an outermost dimension, such as its radius about 21 millimeters. (In this case the ratio is about three).

Figure 3:
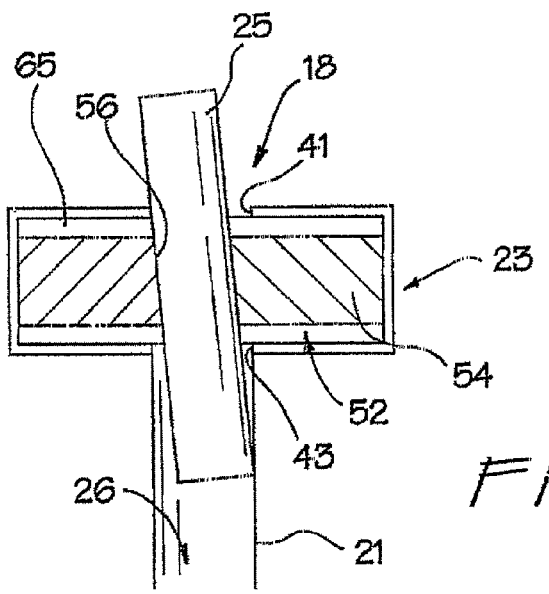
FIG. 3 is an axial cross section view of the trocar illustrating an instrument seal formed during off-axis insertion of the instrument.

Operation of the trocar 18 and associated valve assembly 50 is best illustrated in FIG. 3. In this case, the instrument 25 is illustrated to be inserted off-axis through the opening 56. In this view it can be seen that the portions of the gel material 54 which define the opening 56 of the block 52 also form an instrument seal 61 with the instrument 25. This instrument seal 61 prevents the escape of insufflation gases through the gel block 52 when the instrument 25 is present in the trocar 18.

FIG. 3 illustrates at least two aspects of the present invention, both of which relate to properties of the gel block 52 in the presence of the instrument 25. Initially, it will be noted that the instrument seal (61) will move with the instrument 25. Although the instrument 25 may be inserted along the axis 27, it may also be inserted off-axis or moved off-axis, as illustrated in FIG. 3, during the operation. Under these circumstances, it is important that the instrument seal 61 be maintained, or permitted to "float" with the off-axis movement of the instrument 25. The instrument seal 61 is formed by both the instrument 25 and the valve assembly 50; however, since the instrument 25 will typically be rigid, it is up to the valve assembly 50 to accommodate this flotation.

It is the properties of the gel material 54 which make it particularly desirable for flotation purposes. Properties of the gel material including elongation greater than 1,000 percent, low durometer, and high tear strength, are fully disclosed in the previously mentioned International Application Serial No. PCT/US01/29682.

With the advantages associated with (1) the formation of an instrument seal and a zero seal with a single valve accommodating a wide range of diameters, and (2) the formation of an instrument opening using the instrument itself, it will be appreciated that the concept of this invention will typically be embodied with a structure that is particularly dependent upon the material which forms the access device 18. In a preferred embodiment, the gel material 54 is formed of a KRATON®/oil mixture including a KRATON® tri-block with a styrene-ethylene/butylene-styrene (S-E/B-S) structure in combination with a mineral oil. Other tri-block polymers can be used for this application such as styrene-isoprene-styrene, (S-I-S), styrene-butadiene-styrene (S-B-S), styrene-ethylene/propylene-styrene (S-E/P-S) manufactured under the trademark SEPTON® by the Kuraray Co. These general formulas can be further distinguished by the ratio of the styrene to rubber content: for example, Grade 1650 is a S-E/B-S tri-block with a 29/71 styrene to rubber ratio.

In addition to tri-blocks there are also di-block versions of these materials where styrene is present at only one end of the formula, for example, styrene-ethylene/butylene (S-E/B) di-block.

The various base formulas may also be alloyed with one another to achieve a variety of intermediate properties. For example KRATON® G1701X is a 70% S-E/B 30% S-E/B-S mixture with an overall styrene to rubber ratio of 28/72. It can be appreciated that an almost infinite number of combinations, alloys, and styrene to rubber ratios can be formulated, each capable of providing advantages to a particular embodiment of the invention. These advantages will typically include low durometer, high elongation, and good tear strength.

It is contemplated that the material of the gel block 52 may also include silicone, soft urethanes and even harder plastics which might provide the desired sealing qualities with the addition of a foaming agent. The silicone materials can be of the types currently used for electronic encapsulation. The harder plastics may include PVC, Isoprene, KRATON® neat, and other KRATON®/oil mixtures. In the KRATON®/oil mixture, for example, oils such as vegetable oils, petroleum oils and silicone oils might be substituted for the mineral oil. In the broadest sense, all of these mixtures can be described generally as a gel. The gel will typically have properties including an ability to "flow" which approaches that of a fluid. Particularly in the vicinity of any opening or slit 56 extending through the access device 18, propagation of the opening may be of concern. Stresses resulting from the presence of an instrument will be concentrated at the ends of such an opening or slit. For this reason, a good tear resistance is desired for the gel material. Such a tear resistance is often inherent in the KRATON®/oil mixtures and may be enhanced by encapsulating the gel in other materials. For example, a low tear resistant gel could be encapsulated in a urethane sheath to improve the tear resistant qualities of the resulting products. Such a sheath need not be elastic but could be comprised, for example, of overlapping sheets of a non-elastic material.

Any of the gel materials contemplated could be modified to achieve different properties such as enhanced lubricity, appearance, and wound protection, or to provide anti-cancer or anti-microbial activity. Additives can be incorporated directly into the gel, for example in the case of pharmaceuticals, or applied as a surface treatment to the gel, for example, to improve lubricity or appearance. Other compounds could be added to the gel to modify its physical properties or to assist in subsequent modification of the surface by providing bonding sites or a surface charge. Antioxidants and antirads can be added to the mixture to extend the shelf life of the finished product or increase its ability to withstand radiation sterilization.

Sealing materials used in medical access devices of the past have been chosen primarily for their durometer and elongation. It is these properties which measure the ability of the material to move into small spaces and crevices as may be required to form an instrument seal across the working channel of a trocar. For example, in the past, a silicone mixture was used in medical valves. This mixture had the following properties: an ultimate elongation less than about 1000 percent and a durometer not less than about 5 Shore A.

These properties of the prior art materials are far exceeded by the properties associated with the present invention which in some respects provide a full magnitude of advantage. In fact, the difference between the materials of the prior art and the materials of the present invention are sufficiently substantial, that it is perhaps misleading to refer to the present material as merely a gel. Accordingly, the material of the present invention, having properties including an ultimate elongation greater than about 1000 percent and a durometer less than about 5 Shore A, will be referred to herein as an "ultragel."

In a preferred embodiment of the present invention, the ultragel includes KRATON® and mineral oil and provides a sealing material with the following properties: an ultimate elongation exceeding about 1500 percent, and a durometer of less than about 200 Bloom. The durometer in this case is considerably lower than that of the prior art materials. In fact, the durometer of the present material is so soft it cannot even be measured on the Shore A scale.

The resulting elongation and durometer of the present material facilitates its use with as an access valve which is capable of forming seals with a full range of instrument sizes, but is also capable of functioning as a zero seal. Whereas access devices of the prior art may have required as many as six separate seals in order to accommodate a full range of instrument sizes, access devices can now be made with only a single valve formed of the ultragel material.

In a typical manufacturing process, the KRATON® G1651 is mixed with the mineral oil in a ratio by weight of 1 to 9. In order to manufacture this material, the combination is heated to a temperature of about 200° centigrade. In a preferred method of manufacturing, the mold is provided with a circumferential ring insert which is molded into the gel, and slit inserts which can be removed from the gel to form the opening or slit 56. The resulting gel can be coated with cornstarch to reduce tack and cooled at room temperature.

Many of the properties of the KRATON®/oil mixture will vary with adjustments in the weight ratio of the components. In general, the greater the percentage of mineral oil, the more fluid the mixture; the greater the percentage of KRATON®, the more rigid the material. Weight ratios of KRATON® to oil as low as 1 to 5 have been contemplated for a more rigid structure. As the KRATON®/oil weight ratio approaches 1 to 10, the mixture becomes more liquid. Ratios as high as 1 to 15 have been contemplated for this invention.

The processing temperature can also vary considerably as it is primarily dependent on the type of KRATON® used. Temperatures in a range of about 150° centigrade to about 250° centigrade have been contemplated.

With an appreciation that these ratios and temperatures can develop considerably different properties, it is now apparent that these materials can be layered to provide generally different properties within each layer. For example, an outer layer might be formed of a KRATON®/oil mixture having more rigid properties, thereby providing the gel block 52 with an outer layer that is more rigid. After that layer is at least partially cured, another layer of the material can be poured inside of the outer layer. This second layer might be softer providing the gel block 52 with the significant sealing properties. It has been found that successive layers will tend to fuse slightly at their interface, but will generally maintain their separate identities. Additional layers could be added to provide a progression of properties in a particular device.

Another aspect of the invention associated with insertion of the instrument 25 relates to movement of the gel material 54 as the opening 56 is spread by the instrument 25. As this opening 56 enlarges, the displaced gel material, which is generally non-compressible, will attempt to expand. In order to accommodate this expansion, it is desirable to provide air pockets or voids 65 into which the gel material 54 can move. These voids 65 are most prominently illustrated in FIG. 2A in the absence of the instrument 25.

Figure 4:
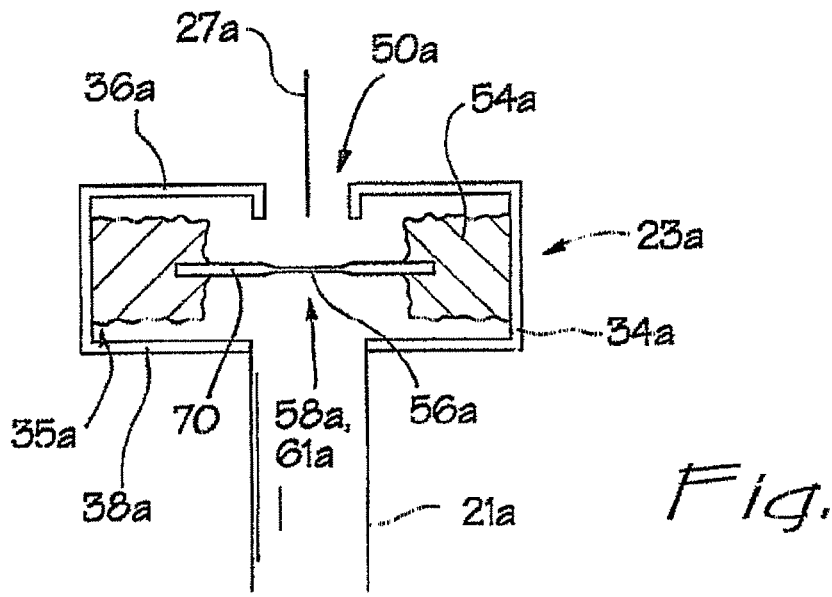
FIG. 4 is an axial cross section view of another embodiment of the invention including a septum seal and a floating gel support.

Another embodiment of the invention is illustrated in FIG. 4. In this embodiment, elements of structure similar to those previously discussed will be designated with the same reference numeral followed by the lower case letter "a." Thus the cannula is designated with the reference numeral 21a, the valve housing with the numeral 23a, and the valve assembly with the number 50a. In this embodiment, the valve assembly 50a includes a thin septum 70 with the opening 56a disposed generally along the axis 27a. The septum 70 will typically be formed of an elastomeric material and will be supported within the valve housing 23a by the gel material 54. In this case, the septum 70 is responsible for the zero seal 58a as well as the instrument seal 61a.

The gel material 54 forms a seal with the septum 70 as well as the housing seal 55a with the housing wall 34a. It will be noted that in this embodiment, the gel material 54 provides floating support for the septum 27. Any outward expansion required of the gel material can be accommodated by the voids 65a between the gel material 54 and the horizontal walls 36a and 38a.

Figure 5:
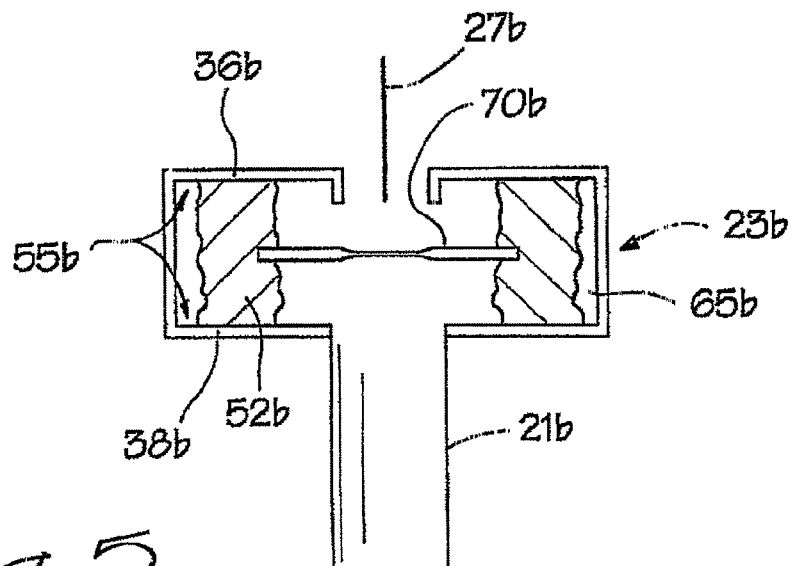
FIG. 5 is an axial cross section view of another embodiment of the valve apparatus.

A further embodiment of the invention is illustrated in FIG. 5, wherein elements of structure similar to those previously disclosed are designated with the same reference numeral followed by the lower case letter "b." The embodiment of FIG. 5 differs from that of FIG. 4 primarily in the location of the gel block 52b. In this case, the housing seal 55b is formed around the axis 27b between the gel block 52 and the horizontal walls 36b and 38b of the valve housing 23b. The voids 65b desired for expansion of the gel block 52b can be located between the vertical wall 34b and the gel block 52b. This embodiment could include the elastomeric septum 70b, or might comprise only the gel block 52b as illustrated in the embodiment of FIG. 2A.

Figure 6:
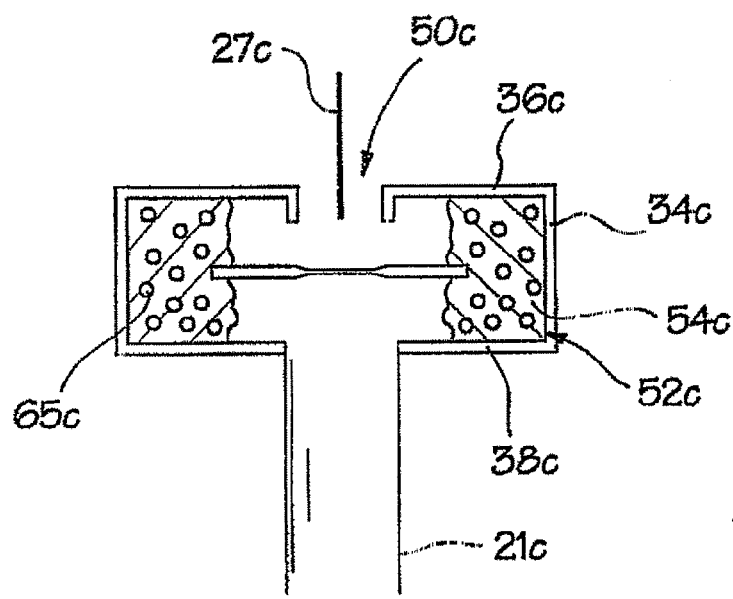
FIG. 6 is an axial cross section view of a valve apparatus with gel material including air pockets.

Another embodiment of the invention is illustrated in FIG. 6, wherein elements of structure similar to those previously disclosed are designated with the same reference numeral followed by the lower case letter "c." In this embodiment, which may include the septum 70c, the block 52c of gel material 54c forms the housing seal 55c around the axis 27c with each of the housing walls 34c, 36c, and 38c. The expansion voids 65c can be formed as air pockets within the gel material 54c of the block 52c. In such an embodiment, the block 52c is generally compressible, like a sponge, as the gel material 54c can expand into the voids 56c to reduce the volume of the block 52c. With this compressibility, flotation of the valve assembly 50c, can be greatly increased with respect to the axis 27c.

Figure 7:
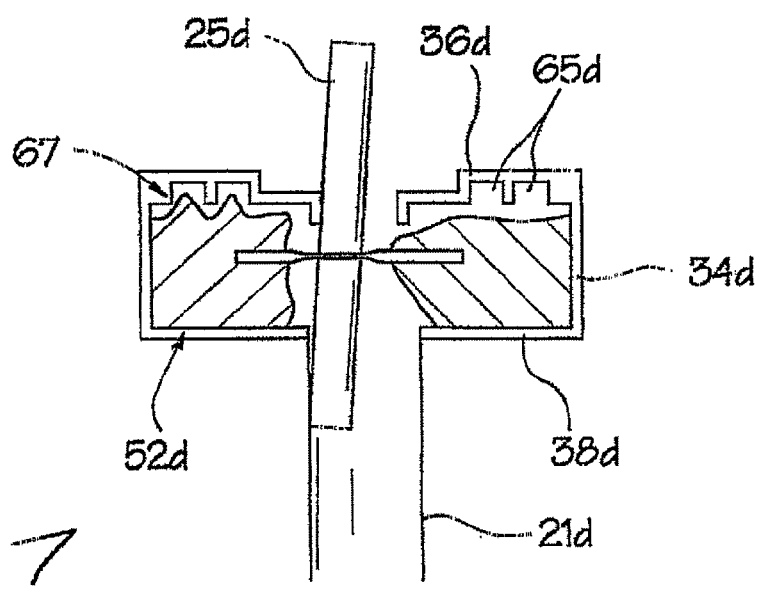
FIG. 7 is an axial cross section view of a further embodiment illustrating air pockets formed in the seal housing.

In the embodiment of FIG. 7, elements of structure similar to those previously disclosed are designated with a the same reference numeral followed by the lower case letter "d." This embodiment differs from those previously disclosed in that the voids 65d are formed permanently within the walls of the housing 23d. For example, the voids 65d can be formed in the horizontal wall 36d to accommodate upward expansion of the gel block 52d, as illustrated by an arrow 67. In this embodiment, the elastomeric septum 70 is insert molded with the gel block 52d, and the housing seal 55 is formed between the gel block 52d and the walls 34d and 38d.

Having disclosed these particular embodiments, it will be understood that many modifications can be made without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

What is claimed is:

1. A surgical access device comprising:
   a valve housing;
   a valve assembly comprising:
      gel material disposed in the valve housing, the gel material defining a housing seal with the valve housing preventing insufflation gas flow therethrough; and
      a septum valve disposed between the gel material and the valve housing and positioned within an opening extending through the gel material, the septum valve arranged to seal against an outer surface of an instrument when the instrument is inserted through the septum valve and to float to accommodate instruments inserted off-axis or instruments moved off-axis.

2. The device of claim 1 wherein the valve housing further comprises an upper wall covering portions of the gel material.

3. The device of claim 2 wherein the upper wall is perpendicular to an inside wall of the valve housing and extending over a portion of the gel material.

4. The device of claim 3 wherein the gel material contacts the inside wall.

5. The device of claim 2 wherein the upper wall has at least one void.

6. The device of claim 2 wherein the upper wall has an opening extending therethrough, the opening in the upper wall aligned with an opening in the septum valve.

7. The device of claim 2 wherein the upper wall has at least one void positioned on either side of the opening in the upper wall.

8. The device of claim 2 wherein the gel material contacts the upper wall.

9. The device of claim 8 wherein the valve housing further comprises a lower wall opposing the upper wall and the gel material contacts the lower wall.

10. The device of claim 2 further comprises an elongate cannula extending from the valve housing.

11. The device of claim 10 wherein the valve housing further comprises a lower wall opposing the upper wall and contacting the elongate cannula.

12. The device of claim 11 wherein the valve housing further comprises an inside wall perpendicular to the upper and lower wall.

13. The device of claim 12 wherein the gel material contacts one of the upper, lower or inside wall of the valve housing.

14. The device of claim 1 wherein the gel material is non-compressible.

15. The device of claim 1 wherein the thickness of the gel material is greater than a thickness of the septum valve.

16. The device of claim 1 wherein the septum valve is made of a material different from the gel material.

17. The device of claim 1 wherein the gel material comprises a di-block or tri-block co-polymer and an oil.

18. The device of claim 1 wherein the gel material is smaller in width than the septum valve.

* * * * *